United States Patent
O'Neil et al.

[19]

[11] Patent Number: 6,126,693
[45] Date of Patent: Oct. 3, 2000

[54] TAPPED BOX FEMORAL STEM ATTACHMENT FOR A MODULAR KNEE PROSTHESIS

[75] Inventors: Michael O'Neil, West Barnstable; Arnold Oyola, Taunton, both of Mass.

[73] Assignee: Depuy Orthopaedics, Inc., Warsaw, Ind.

[21] Appl. No.: 09/156,112

[22] Filed: Sep. 18, 1998

[51] Int. Cl.[7] ....................................................... A61F 2/38
[52] U.S. Cl. .............................................................. 623/20
[58] Field of Search .................................................. 623/20

[56] References Cited

U.S. PATENT DOCUMENTS

| | | | |
|---|---|---|---|
| 5,133,760 | 7/1992 | Petersen | 623/20 |
| 5,147,406 | 9/1992 | Houston | 623/20 |
| 5,258,032 | 11/1993 | Bertin | 623/20 |
| 5,556,433 | 9/1996 | Gabriel | 623/20 |
| 5,683,472 | 11/1997 | O'Neil | 623/20 |
| 5,824,097 | 10/1998 | Gabriel | 623/20 |
| 5,879,391 | 3/1999 | Slamin | 623/20 |
| 5,879,394 | 3/1999 | Ashby | 623/20 |
| 5,944,756 | 8/1999 | Fischetti | 623/20 |

*Primary Examiner*—Michael J. Milano
*Attorney, Agent, or Firm*—Nutter, McClennen & Fish, LLP

[57] ABSTRACT

The present invention provides a knee prosthesis having a femoral component having a pair of spaced apart condylar portions and a boss structure extending between the condylar portions. The knee prosthesis also includes a stem component having a proximal end and a distal end. The knee prosthesis further includes a lock nut for securing the stem member to the femoral component.

14 Claims, 6 Drawing Sheets

TAPPED BOX FEMORAL STEM ATTACHMENT FOR A MODULAR KNEE PROSTHESIS

CROSS-REFERENCE TO RELATED APPLICATIONS

Not applicable.

STATEMENT REGARDING FEDERALLY SPONSORED RESEARCH

Not applicable.

FIELD OF THE INVENTION

The invention relates to medical devices, and more particularly to prosthetic joint components.

BACKGROUND OF THE INVENTION

Joint arthroplasty is a well-known surgical procedure by which a diseased and/or damaged natural joint is replaced by a prosthetic joint. A typical knee prosthesis includes a tibial component, a femoral component, a femoral stem assembly, and a patellar component. The femoral component generally includes a pair of spaced apart condylar portions, the superior surfaces of which articulate with a portion of the tibial component. The femoral stem assembly provides lateral stability, and it typically includes a member that is inserted within a reamed intramedullary canal at the distal end of a femur. The stem is typically coupled to the femoral component by a collar and bolt through a bore or opening which extends completely through the femoral component.

Although modular systems can provide an advantageous reduction in joint component inventory, known systems do not fully address the problems associated with variations in intramedullary canal geometry. Specifically, the variations in the morphology of the intermedullary canal often do not match the geometry of the stem, forcing the surgical positioning of the femoral component that is mated to the stem to be determined by considerations other than the shape of the canal.

For example, if the implant geometry does not match the canal geometry, the stem of the implant can contact the cortical wall of the intramedullary canal while the stem is being impacted. This problem can be further complicated when a femoral stem is mated to a sleeve that increases the effective length of the stem so that it is in a bowed portion of the intramedullary canal.

In response to the above problems, a surgeon may be forced to remove the stem (or entire component) and replace it with a stem having a smaller diameter or shorter length, even if the replacement stem is thought to be less suitable than the original stem, but for the improper fit. Also, the surgeon may have to cut notches in the femur to accommodate a shifted femoral component.

Furthermore, known prosthesis attachment systems can cause additional problems related to the production of wear debris and third body particulates. Since known systems employ a stem which is typically attached to the femoral component through a bore which extends completely through the femoral component, any wear debris or particulates produced are able to easily migrate into the joint. The phenomenon of wear debris within artificial joints is a serious problem that can inhibit the proper mechanical functioning of the joint. If wear debris develops within an artificial joint, it must usually be corrected by surgical removal of the debris or by subsequent replacement of the artificial joint.

Therefore, despite the existence of joint prostheses having modular components, there remains a need for a modular joint prosthesis that has greater versatility to accommodate differing patient anatomy and joint conditions and reduces the possibility of wear debris and particulate migration and production.

BRIEF SUMMARY OF THE INVENTION

The present invention relates to a modular knee joint prosthesis having improved versatility. Components of the modular prosthesis of the invention are able to be used with both right and left side prostheses.

The present invention provides a modular knee prosthesis which includes a femoral component having a pair of spaced apart condylar portions and a boss structure extending between the condylar portions. The boss structure has a threaded blind cavity formed within a superior surface of the boss structure. The knee prosthesis further includes a stem component which has a proximal end and a threaded distal end that is effective to matingly engage the blind cavity.

A mounting surface may be provided which is integrated into the femoral component boss structure for varying the angulation of the stem component relative to the femoral component. The mounting surface is oriented substantially transverse to a longitudinal axis of the stem member when the stem member is mounted thereon such that an engaging surface of the stem component and a superior surface of the boss structure define a selected mounting angle therebetween. Finally, the knee prosthesis includes a lock nut positioned between the stem member and femoral component to secure the stem member to the femoral component at various orientations.

BRIEF DESCRIPTION OF THE DRAWINGS

A more complete understanding of the present invention and the attendant advantages and features thereof will be more readily understood by reference to the following detailed description when considered in conjunction with the accompanying drawings wherein.

DETAILED DESCRIPTION OF THE INVENTION

Figure 1:
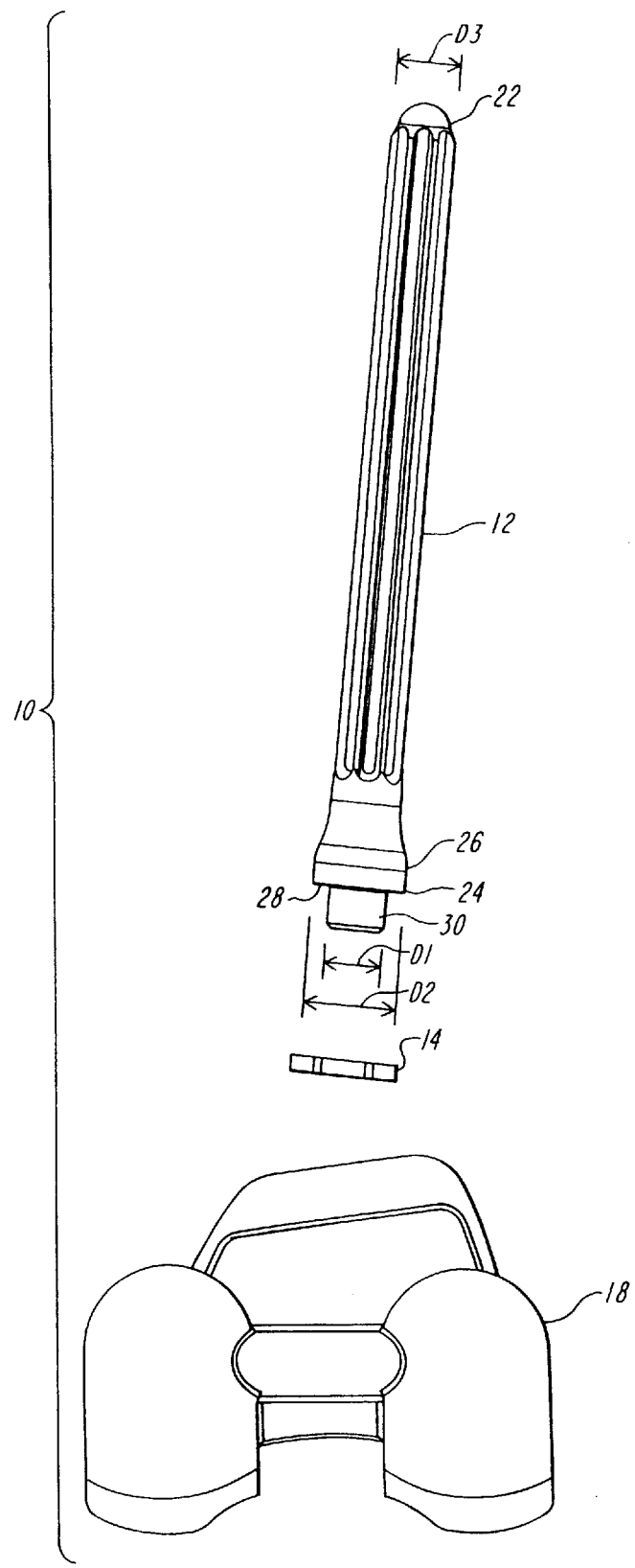
FIG. 1 is an exploded view of a multi-piece prosthetic joint component system.

FIG. 1 is an exploded view of a modular prosthetic joint prosthesis 10 that includes a number of modular components including an elongate stem member 12, a lock nut member 14, and a femoral component 18. The construction of the present invention provides several mounting possibilities that are compatible with the various possible orientations of the femoral stem when mounted within the distal portion of the femur.

Referring again to FIG. 1, the stem 12 has a proximal end 22 and a distal end 24 with a bulged or flared portion 26 disposed between the proximal and distal ends 22, 24. The bulged portion 26 includes a distally facing surface 28 which forms a mating shoulder adapted for mating with the lock nut 14 or alternatively, directly with the femoral component 18 as discussed in more detail later herein. The distal end 24 of the stem 12 includes a connector portion 30 which extends distally from distally facing surface 28. The connector portion 30 has threads 29 formed thereon effective to threadably engage either or both the lock nut 14 and femoral component 18, as discussed in more detail later herein.

In an exemplary embodiment, the connector portion 30 of stem 12 has an outer diameter (D1) relatively smaller than the outer diameter (D2) as measured at the bulged portion 26. Preferably, the outer diameter (D3) of the proximal end 22 of stem 12 is also less than the outer diameter (D2) of the bulged portion 26.

In one embodiment of the present invention, the stem 12 may have a degree of offset in the medial-lateral direction with respect to the femoral component. While the embodiment shown and described above allows for offset in either direction of the medial-lateral plane, offset placement may also be provided in the anterior-posterior direction, and virtually at any position between medial-lateral and anterior-posterior.

Figure 2:
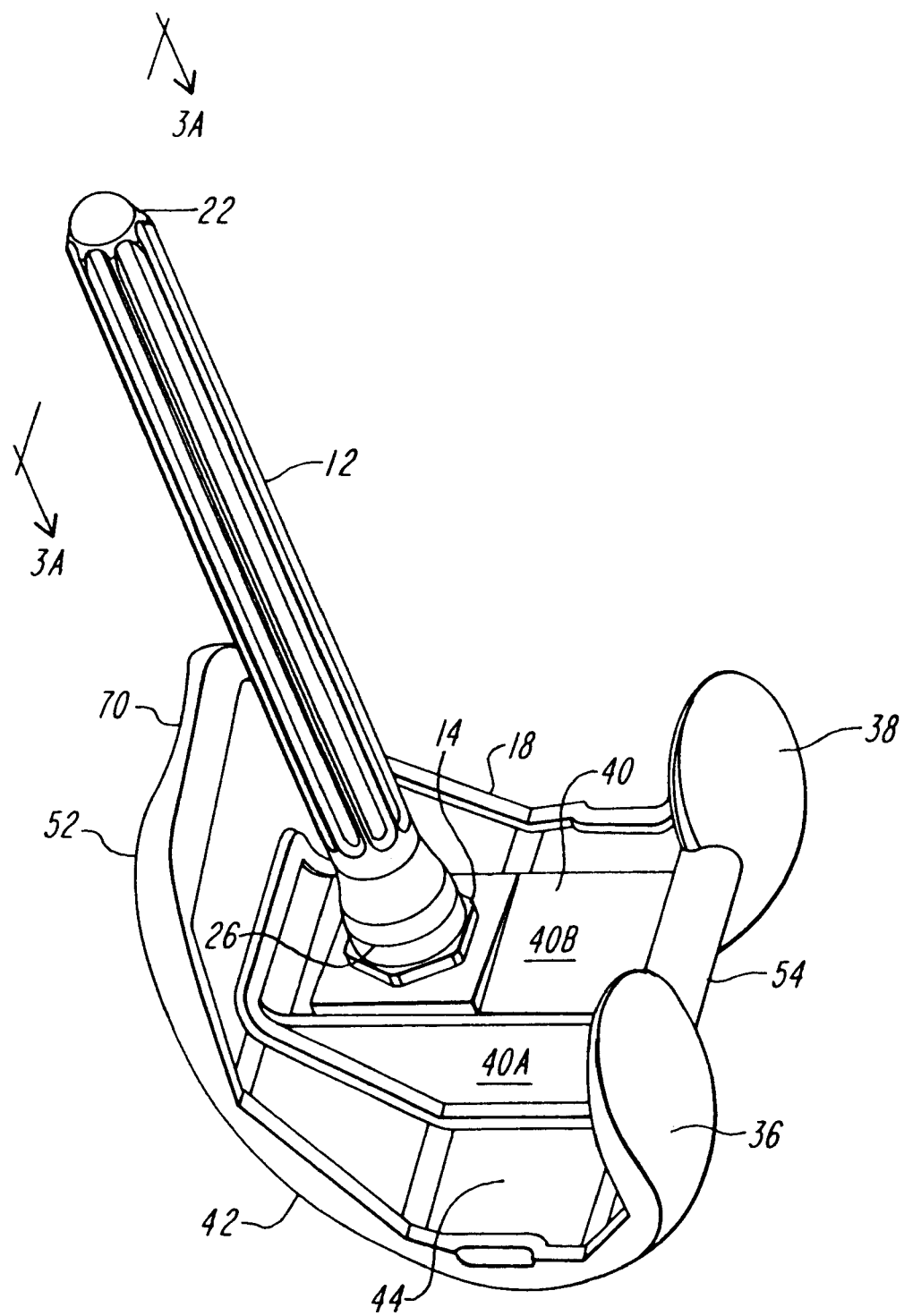
FIG. 2 is an assembled view of the joint component system shown in FIG. 1.

Referring to FIG. 2, the femoral component 18 has a pair of condylar portions 36, 38 that are connected by an inter-condylar boss or box structure 40. The femoral component 18 has an articulation surface 42, an opposed surface 44 and an anterior side 52 and a posterior side 54. The anterior side 52 of the femoral component 18 includes a patellar groove 70 within which seats a patellar prosthetic component (not shown). The surfaces 42 of the curved condylar portions 36, 38 articulate with a prosthetic tibial component (not shown) mounted on the head of the tibia, in a manner well known to those of ordinary skill in the art.

Referring now to FIGS. 3A–5, the boss structure 40 has a pair of substantially vertical side walls 40A that are connected by a top or superior, seating or mounting surface 40B. The boss structure 40 further has a blind cavity 46 formed therein which extends from the top superior surface 40B partially towards an inferior surface 40C of the boss structure 40. The cavity 46 is further defined by sidewalls 48 bounded at a distal end by a substantially horizontal end wall 50. Preferably, the cavity 46 is not open to the inferior or articulation surface 42 of the femoral component 18 thereby preventing the migration therethrough of any wear debris or third body particulates which may be produced by the prosthesis.

The shape of the cavity 46 may be elliptical, oval, spherical or of any other suitable shape so as to accommodate the distal end of the stem 12. Once the prosthesis is assembled, the cavity 46 accepts and mates with the distal end of the stem 12 so that the stem 12 is secured at a desired orientation, as discussed in more detail later herein. Female threads may be formed within the cavity 46 to engage corresponding male threads 29 formed on the distal connector portion 30 of the stem member 12.

Figure 3A:
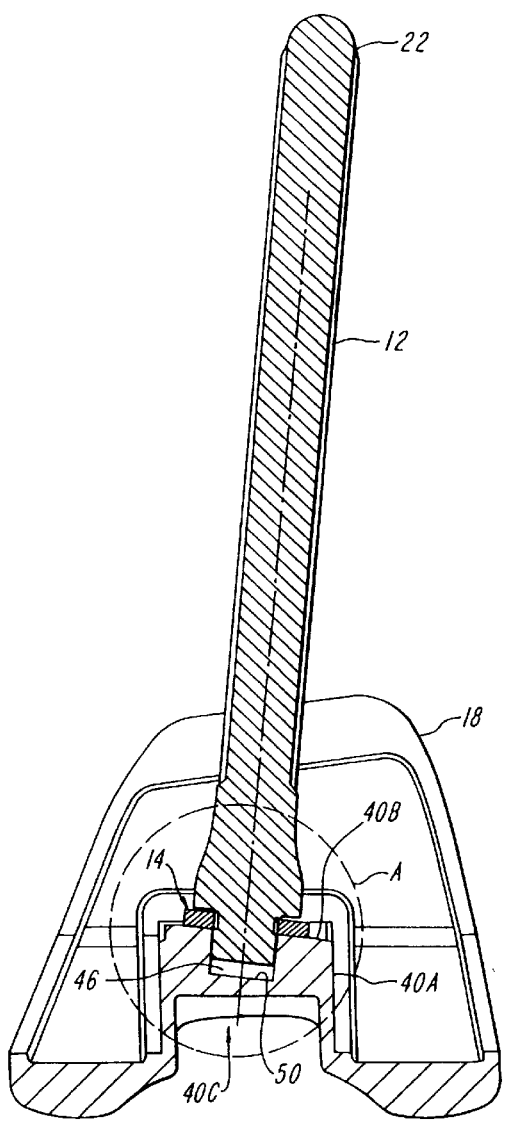
FIG. 3A is a sectional view of the joint component system taken along line 3A—3A in FIG. 2.
Figure 3B:
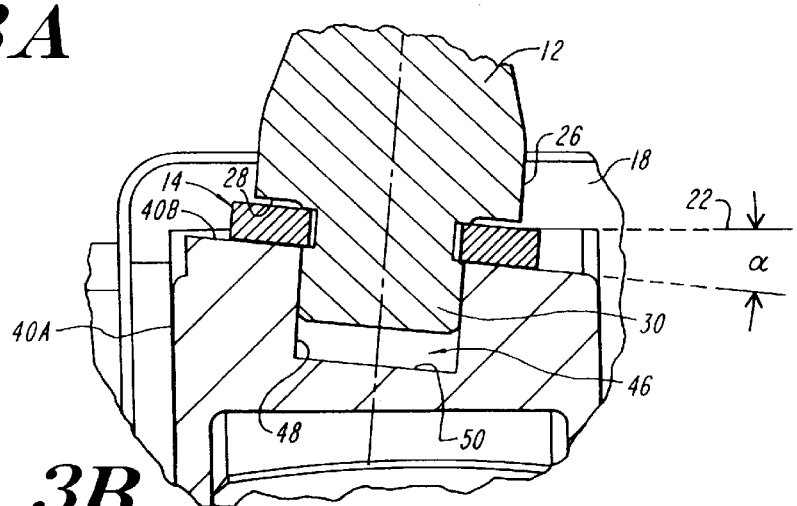
FIG. 3B is a detailed view of portion A in FIG. 3A.
Figure 4:
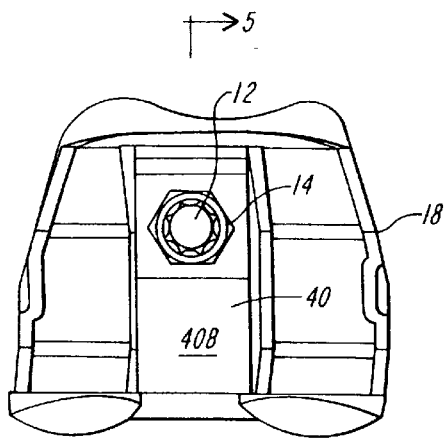
FIG. 4 is a top view of the joint component system of FIG. 1.
Figure 5:
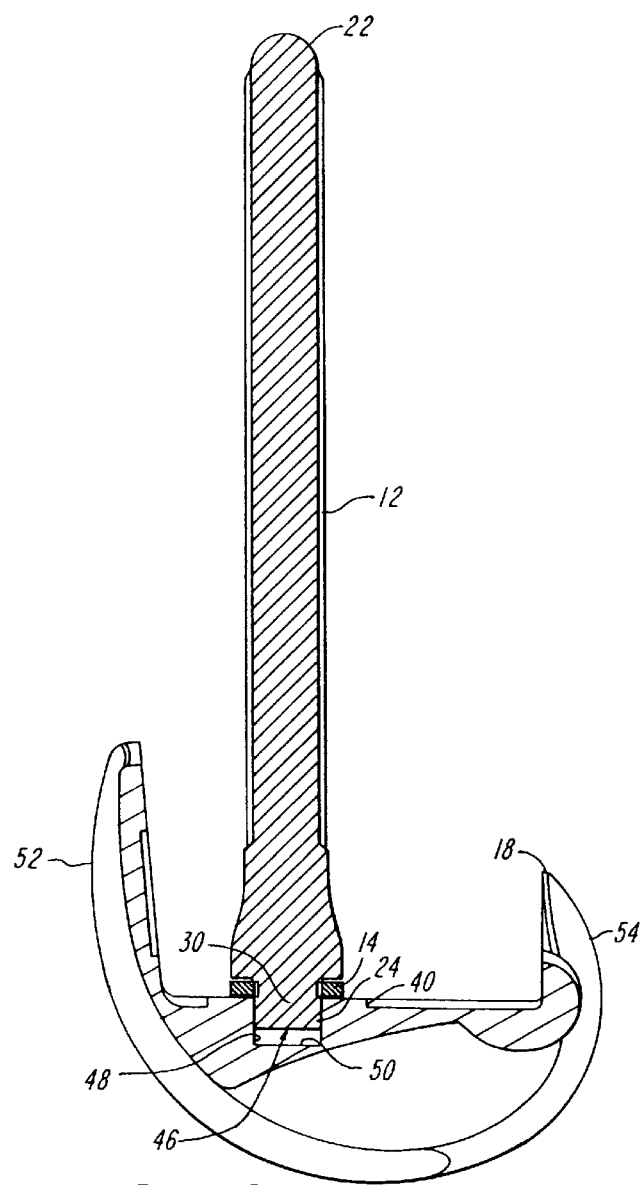
FIG. 5 is a sectional view of the joint component system taken along line 5—5 in FIG. 4.

Referring to FIGS. 3A–3B, in an exemplary embodiment, a portion of the superior surface 40B of the boss structure 40 is canted and forms an angle with a transverse plane 22. The distally facing surface 28 of stem member 12 and the top superior surface 40B of boss structure 40 may then form a mounting angle (α) when the stem is assembled with the femoral component 18 and engages the boss top surface 40B. The angle (α) is preferably between about 1° and about 15°.

According to one practice of the invention, the boss engaging surface 40B can be canted in the anterior-posterior direction to either the anterior or posterior side as measured in the sagittal plane. Likewise, the surface 40B can be canted in the medial-lateral direction to either the medial side or the lateral side as measured in the coronal plane. Preferably, the angle (α) can range between about 1° and about 15° in any direction. This varied angulation provides a plurality of stem mounting angles which is compatible with the various possible orientations of the femoral stem when mounted within the distal portion of the femur. The boss mounting surface 40B can be configured to provide any combination of coronal and sagittal plane angulations that are constrained by the foregoing angle ranges.

Figure 6A:
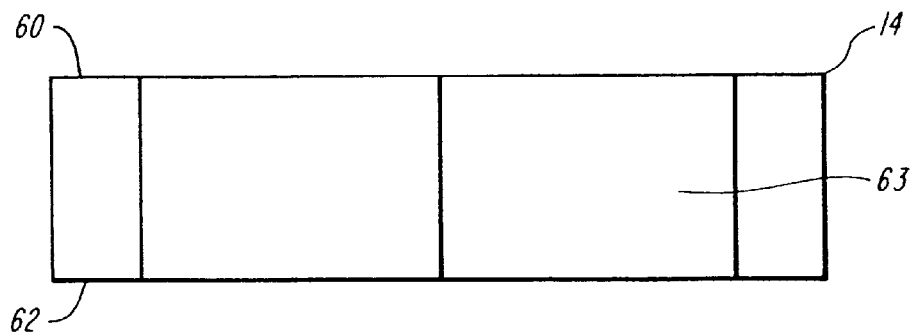
FIG. 6A is a side view of the lock nut member of FIG. 1.
Figure 6B:
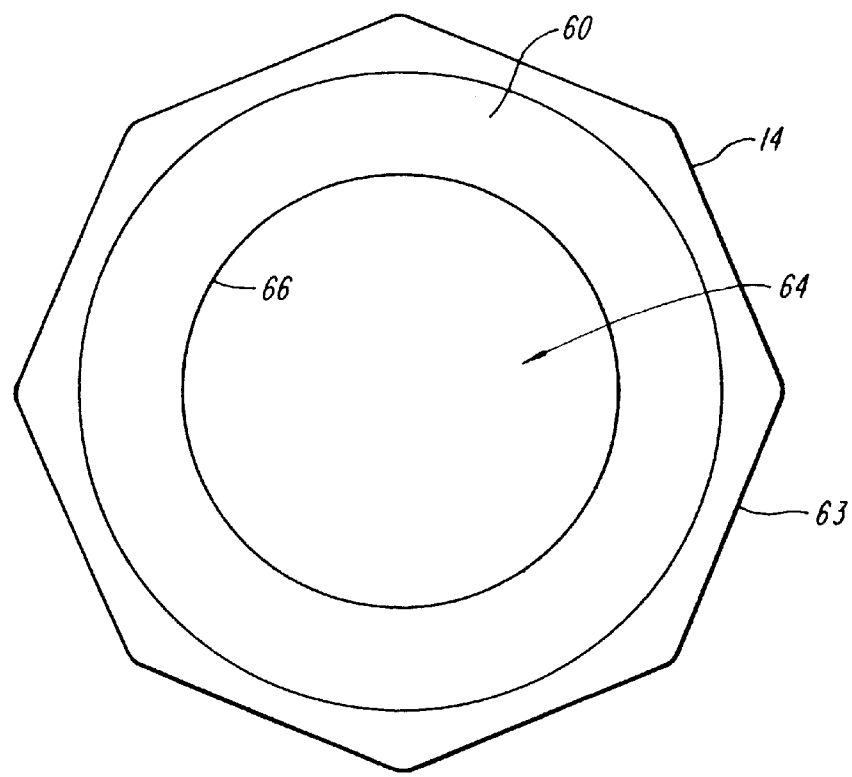
FIG. 6B is a top view of the lock nut member of FIG. 6A.

FIGS. 6A and 6B illustrate the lock nut 14 useful with the present invention. The nut 14 includes generally opposed top and bottom portions 60, 62 bounded by substantially vertical sidewalls 63. A central aperture 64 extends between the opposed top and bottom portions 60, 62. Preferably, threads are formed within an inner surface 66 of the nut 14 effective to threadably engage corresponding threads formed on the distal end of the stem 12. The bottom portion 62 is adapted to mate with and engage the superior surface 40B of the boss structure 40 when the components of the prosthesis are assembled. The lock nut 14 can be composed of any biocompatible material such as cobalt/chromium or titanium alloy, stainless steel, ultra-high molecular weight polyethylene or high density polyethylene.

Figure 7:
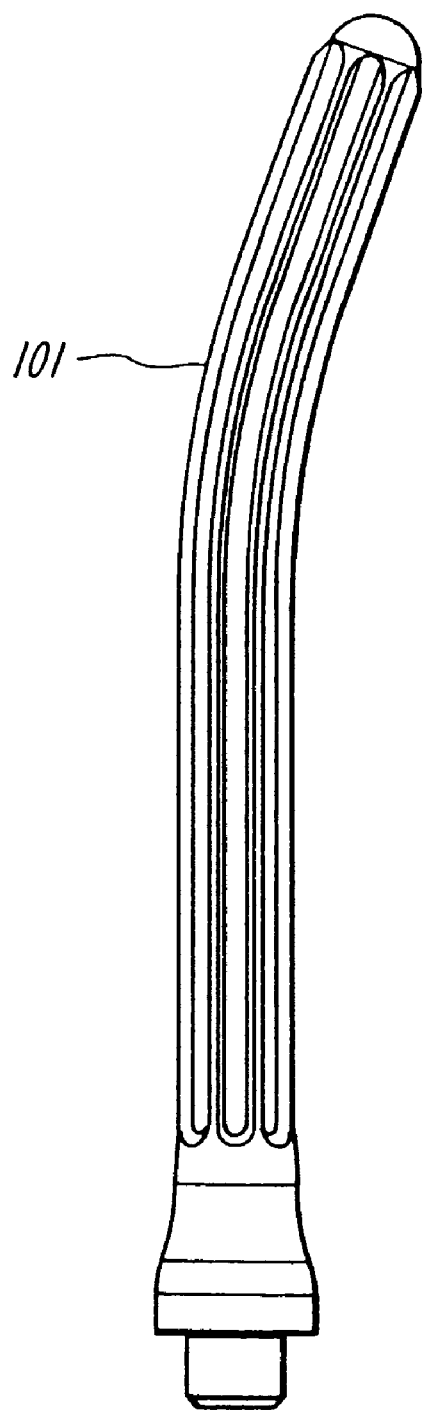
FIG. 7 is an exploded view of a bowed stem member.

As described above, the stem 12 and the femoral component 18 cooperate to secure the stem 12 to the femoral component 18. When a straight or non-bowed stem is used, the direct connection between the stem and femoral component is typically sufficient to adequately secure the stem without overloading the stem. However, when a bowed stem 101 (see FIG. 7) is used, the lock nut may be required to lock the bow placement with respect to the medial-lateral or anterior-posterior plane of the femoral component.

Referring to FIGS. 1–5, an exemplary modular knee prosthesis utilizing the components described above can be assembled in the following manner. The lock nut 14 is positioned on the superior surface 40B of the boss structure 40 such that the lock nut aperture 64 is aligned with cavity 46. Alternatively, the lock nut 14 may be prethreaded directly on the distal end of the stem member 12. The stem 12 is mated to the lock nut 14 by positioning the distal connector portion 30 through nut aperture 64 so that the mating surface or shoulder 28 rests upon the top surface 60 of the nut 14. The distal end 24 of stem 12 is positioned such that at least a portion of the connector end 30 protrudes and extends into box cavity 46. The connector end 30 of stem 12 is rotated into threadable engagement with the cavity 46. The lock nut 14 may be tightened to threadably engage the distal connector portion 30 of the stem 12 to the femoral component 18.

The lock nut 14 allows mounting of preferably, a bowed stem within the cavity 46 at an angle that is determined by a surgeon. In addition, the threaded connector portion 30 of the distal end of the stem 12 threadably engages the threaded box cavity 46 and fixedly secures the stem 12 to the femoral component 18. In this axially successive assemblage, the lock nut is positioned between the stem and boss by the threaded engagement of the lock nut, stem and cavity. The lock nut may then be turned down onto the boss structure to secure the stem at a desired orientation.

A variety of modifications and variations of the present invention are possible in light of the above teachings. It is also understood that the basic femoral component construction in the present system can be used for either the right or left knee. All references cited herein are expressly incorporated by reference in their entirety.

What is claimed is:

1. A modular knee prosthesis comprising:
    a femoral component having a pair of spaced apart condylar portions and a boss structure extending between the condylar portions, the boss structure having a cavity formed within a superior surface thereof;
    an elongate stem having a proximal and a distal end, wherein the distal end is mateable with the cavity of the first component; and
    a lock nut for securing the elongate stem to the femoral component,
    wherein a portion of the distal end of the stem is threaded, the cavity has threads formed therein and the lock nut has threads formed therein both for threadably engaging the distal end of the stem.

2. The knee prosthesis of claim 1, wherein the distal end of the stem component is offset a selected distance in the medial lateral direction towards the medial side of the prosthesis.

3. The knee prosthesis of claim 1, wherein the distal end of the stem component is offset a selected distance in the medial lateral direction towards the lateral side of the prosthesis.

4. The knee prosthesis of claim 1, wherein the distal end of the stem component is centered in the medial lateral direction.

5. The knee prosthesis of claim 1, wherein the elongate stem is bowed.

6. The knee prosthesis of claim 1, wherein the distal end of the stem includes a distally facing surface mountable on a superior surface of the boss structure, the stem mounting surface of the second component and the superior surface of the boss structure defining a selected mounting angle therebetween.

7. The knee prosthesis of claim 6, wherein the mounting angle of the mounting surface of the second component is in the range of 1° to about 15° in the medial-lateral direction in the transverse plane, to the medial or lateral side.

8. The knee prothesis of claim 7, wherein the lock nut is positionable between the stem component and the femoral boss structure.

9. A modular knee prosthesis comprising:
    a femoral component having a pair of spaced apart condylar portion and a boss structure extending between the condylar portions the boss structure having a superior mounting surface with a cavity formed therein, the cavity defined at one end by a substantially horizontal endwall;
    a stem component having a proximal end and a distal end which is mateable with the boss cavity; and
    a lock nut positionable between the femoral component and stem component for securing the stem member to the femoral component,
    wherein the superior mounting surface of the boss structure is canted relative to a traverse plane, and wherein at least a portion of the distal end of the stem component is threaded.

10. The knee prosthesis of claim 9, wherein the stem component is bowed.

11. The knee prosthesis of claim 9, wherein the cavity has threads formed therein.

12. The knee prosthesis of claim 11, wherein the distal end of the stem component has threads formed thereon effective to threadably engage the cavity threads.

13. A modular knee prosthesis comprising:
    a femoral component having a pair of spaced apart condylar portion and a boss structure extending between the condylar portions, the boss structure having a superior mounting surface with a cavity formed therein, the cavity defined by threaded interior sidewalls which are connected at a distal end by a substantially horizontal endwall;
    a stem component having a proximal end and a threaded distal end which is threadably engageable within the boss cavity, the stem component having a portion disposed proximate the distal end, the portion forming a distally facing mounting shoulder; and
    a lock nut positionable between the femoral component and stem component for securing the stem member to the femoral component, wherein the distally facing mounting shoulder and superior mounting surface of the boss structure define a selected mounting angle therebetween.

14. The knee prosthesis of claim 13, wherein the mounting angle is between about 1° and about 15°.

* * * * *